United States Patent [19]

Hanisch

[11] Patent Number: 4,551,541

[45] Date of Patent: Nov. 5, 1985

[54] ORGANOSILANE ESTERS HAVING GLYCOL ETHER MOIETIES

[75] Inventor: Horst Hanisch, Hennef/Sieg, Fed. Rep. of Germany

[73] Assignee: Dynamit Nobel Aktiengesellschaft, Troisdorf, Fed. Rep. of Germany

[21] Appl. No.: 462,863

[22] Filed: Feb. 1, 1983

[30] Foreign Application Priority Data

Feb. 4, 1982 [DE] Fed. Rep. of Germany ....... 3203688

[51] Int. Cl.$^4$ ........................... C07F 7/08; C07F 7/10; C07F 7/18
[52] U.S. Cl. .................................. 549/215; 556/424; 556/429
[58] Field of Search ................. 556/424, 429; 549/215

[56] References Cited

U.S. PATENT DOCUMENTS

| | | | |
|---|---|---|---|
| 2,541,154 | 2/1951 | Clapsadle | 556/424 |
| 3,317,577 | 5/1967 | Ryan | 556/424 X |
| 3,691,222 | 9/1972 | Wendel | 556/429 X |
| 3,692,812 | 9/1972 | Berger | 556/429 |
| 3,847,860 | 11/1974 | Seiler et al. | 556/424 X |
| 4,012,403 | 3/1977 | Mui | 556/429 |
| 4,059,473 | 11/1977 | Okami | 556/429 X |

*Primary Examiner*—Paul F. Shaver
*Attorney, Agent, or Firm*—Felfe & Lynch

[57] ABSTRACT

The present invention relates to new organosilane esters which can be characterized by the formula Y-$(CH_2)_n Si(CH_3)_p$-$X_m Z_{3-(m+p)}$. In this formula, Y represents either a substituted or unsubstituted amino group, or it represents the mercapto moiety or the moiety

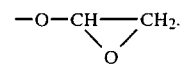

X represents an alkoxy group with 1 to 4 carbon atoms and Z a glycol ether moiety. The index n can assume the numerical values from 1 to 3, m can be 0 or 1 and p can be 0 or 1 or 2, on the condition that m+p is equal to or less than 2. The new silanes yield very stable hydrolyzates and have good adhesion-improving properties. They are therefore particularly well suited for use in sealing compositions.

12 Claims, No Drawings

ORGANOSILANE ESTERS HAVING GLYCOL ETHER MOIETIES

BACKGROUND OF THE INVENTION

The subject matter of the present invention is new organosilane esters which give improved effectiveness to sealing compositions. The improved effectiveness manifests itself especially in the case of sealing compositions on a polyurethane basis, whose adhesivity and elongation are improved considerably by the addition of these new silanes.

Organosilane esters are known, whose organofunctional groups have a substituted or unsubstituted amino, mercapto or glycidyl moiety, and which contain, as silicon-functional ester groupings, alkoxy moieties whose alkyl grouping is not interrupted by oxygen atoms. Examples of these known organofunctional silane esters are gamma-aminopropyltriethoxysilane, N-beta-aminoethyl-gamma-aminopropyltrimethoxysilane, gamma-mercaptopropyltrimethoxysilane or gamma-glycidyloxypropyltrimethoxysilane.

These known organosilane esters are known to increase adhesion between various polymers and inorganic, oxidic or metallic substrates, such as glass, concrete or aluminum, for example. On the basis of these adhesion-improving properties it has already been proposed to use these silane esters in polyurethane sealing compositions. When these known organosilane esters are used in polyurethane sealing compositions, however, it has been found disadvantageous that their effect does not fully develop until a relatively long time after they have been incorporated. The problem therefore existed of finding organofunctional silane esters which develop their full effectiveness, especially in polyurethane sealing compositions, as soon as possible after they have been incorporated.

As a solution to this problem, organosilane esters have been discovered having the formula:

wherein

Y represents a moiety from group NHR (R=H or $C_{1-6}$ alkyl or phenyl or —(CH$_2$)$_2$—NH$_2$), —SH or

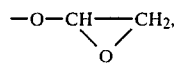

or the grouping —NH—(CH$_2$)$_2$—NH—(CH$_2$)$_2$—NH$_2$

X represents a moiety from the group —OCH$_3$, —OC$_2$H$_5$ and —OC$_3$H$_7$,

Z represents the moiety —O—(CH$_2$—CH$_2$O)$_q$—R′, wherein one of the H-atoms can be substituted by a methyl-group q being able to assume values of 2 or 3 and R′ representing an alkyl of 1 to 4 carbon atoms, and m represents the numbers 0 or 1 or 2, n the numbers 1 or 2 or 3, and p the values 0 or 1, on the condition that m+p is equal to or less than 2.

These new silane esters, when used in polyurethane sealing compositions, attain within a short time after processing very high adhesion and elongation factors, which surprisingly can be twice as high as they are when known organosilane esters are used.

The new organosilane esters can be prepared in a manner known in itself by the transesterification of known organosilane esters with di- or tri-ethylene glycol ethers. The ethylene glycol ether is best used in an excess; it is also possible, however, to use equimolecular amounts. The transesterification is advantageously performed at elevated temperature, preferably at the boiling temperature of the reaction mixture, while the simple alcohol that forms is removed by distillation.

Adequate yields can be obtained in the transesterification performed for the preparation of the aminoalkylsilane esters of the invention without the use of transesterification catalysts. In the preparation of mercapto- and glycidyloxyalkylsilane esters of the invention, however, it is recommendable to add known transesterification catalysts, such as titanic acid esters, for example, in order to obtain sufficient yields of the products in accordance with the invention.

The transesterification product contains, in addition to a small amount of unreacted glycol ether, mostly the completely transesterified organosilane. Depending on how the reaction is conducted and how great an excess of glycol ethers is selected, however, partial organosilane esters of the glycol ethers are also formed. Basically, it is possible to separate these partial esters from the triesters of the glycol ethers by distillation, but for the applications cited, especially use in polyurethane sealing compositions, this separation is not necessary.

Suitable starting products for the preparation of the glycol esters of the invention are the corresponding organofunctional trialkoxysilanes, the alkoxy group being preferably a methoxy or ethoxy group. It is also possible to use the corresponding organochlorosilanes as starting products and esterify them directly with the glycol ethers by methods known in themselves. When using aminosilanes as starting material, one H-atom of the amino group can be substituted by an alkyl group with one or three c-atoms or by an aminoalkyl group, which can also be substituted in the same way. An example is: H$_2$N—(CH$_2$)$_2$—NH—(CH$_2$)$_2$—NH—(CH$_2$)$_3$—S.(OCH$_3$)$_3$.

Glycol ethers which can be used in the preparation of the products of the invention are the di- and tri-ethylene or propylen glycol monoethyl ethers whose ether moieties have 1 to 4 carbon atoms. Examples of such glycol ethers are: diethylene glycol monomethyl ether, diethylene glycol mono-n-butyl ether, triethylene glycol monoethyl ether, triethylene glycol mono-n-butyl ether, diethylene glykol monoethyl ether, isomers of dipropylene glykol mono ethyl ethers and dipropylene glykol mono-iso-propylether.

The organofunctional group of the new silane esters is preferably separated from the silicon atom by three CH$_2$ groups. The number of the methylene groups can, however, be less if, for example, beta-aminoethyltrimethoxysilane is used as starting product.

The new compounds are used either by adding them to the polymers whose adhesivity is to be improved or by applying them to the surface that is to be treated with polymers. When they are used as additives, they are added to the polymers, the sealing compositions for example, in an amount of about 0.5 to 1.5% by weight. It is also possible, however, first to react the compounds with highly reactive organic compounds before adding them to the polymers, and then to use the reaction product as the additive.

The pretreatment of substrates with the compounds of the invention is performed either with the latter dissolved in organic solvents or in the form of aqueous hydrolyzates. The concentration of such solutions or hydrolyzates is not critical. An organosilane ester content between 1 and 5% by weight will generally be selected.

Surprisingly, the new organosilane esters can be used particularly well in the form of aqueous hydrolyzates, since such hydrolyzates are very stable. These hydrolyzates are also easy to prepare, since the compounds of the invention dissolve and undergo hydrolysis in water much more rapidly than the known organosilane esters. On the basis of these good hydrolysis properties, the present compounds can also be hydrolyzed perfectly well in aqueous salt solutions. Even hydrolyzates prepared with a 15% aqueous ammonium sulfate solution are stable for much longer than 14 days.

Substrates suitable for pretreatment with the compounds of the invention are a great number of inorganic-oxidic materials such as, for example, glass in its various forms of fabrication, ceramic, concrete, tiles or metals such as aluminum, magnesium, copper, or alloys containing these metals. Also mineral fillers, especially silicatic fillers, and inorganic pigments such as iron oxides, titanium oxide or zinc oxide, can be pretreated with the compounds of the invention.

The pretreatment of the substrates is performed for the purpose of improving the adhesion between the substrates and a variety of polymers. Fibers, fillers or pigments can be bound into polymers better than they can without the addition of these compounds. This improved action becomes apparent even if only 0.1 wt-% of the silanes of the invention is applied to the above-named substrates.

EXAMPLES

EXAMPLE 1

Transesterification of Gamma-aminopropyltrimethoxysilane with Diethyleneglycol Monomethyl Ether In a stand apparatus equipped with internal thermometer and a reflux condenser with calcium chloride tube and stirrer, 412 g (2.3 mol) of gamma-aminopropyltrimethoxysilane was placed and 1242 g (10.35 mol=50% excess) of diethylene glycol monomethyl ether was added and mixed. The reaction mixture was refluxed for two hours, the boiling temperature being approximately 110° C.

After the reaction mixture had cooled, the reflux condenser was replaced with a distillation bridge. At first the methyl alcohol released in the reaction was distilled off at standard pressure, and then, after another cooling, a vacuum distillation was performed at about 10 mbar to remove unreacted diethylene glycol monomethyl ether until an internal temperature of 130° C. was reached.

979 g of a raw product was obtained, which still contained about 13% of diethylene glycol monomethyl ether by weight. Approximately 75% of the transesterification product consists of tris[-2(2-methoxy-ethoxy)-ethoxy]silyl-3-aminopropane of the formula $H_2N-CH_2-CH_2-CH_2-Si[O(CH_2-CH_2O)_2CH_3]_3$, which was confirmed by gas chromatography and mass spectrometry. The remainder was mostly the corresponding mono- and di-[2-(2-methoxy-ethoxy)-ethoxy]silyl compounds.

EXAMPLE 2

As in Example 1, 221 g (1 mol) of gamma-aminopropyltriethoxysilane was transesterified with 540 g (4.5 mol=50% excess) of diethylene glycol monomethyl ether. The reaction mixture was refluxed for two hours. The boiling temperature was approximately 135° C.

As in Example 1, the ethanol was first distilled out at standard pressure and then the excess and unreacted diethylene glycol monoethyl ether was removed with a vacuum of about 10 up down to a temperature in the liquid of 130° C.

The raw product (405 g) obtained in this manner still contained 49 g of the diglycol ether and 75 g (17 wt.-%) of the di[2-(2-methoxy-ethyoxy)-ethoxy]silyl compounds. Approximately 315 g of the tri[2-(2-methoxy-ethoxy)-ethoxy]silyl-3-aminopropane was obtained, and its formula was proven by gas chromatography and mass spectrometry.

EXAMPLE 3

Transesterification of Gamma-aminopropyltriethoxysilane with Diethylene Glycol Monoethyl Ether As in Example 1, 122 g (0.55 mol) of gamma-aminopropyltriethoxysilane was transesterified with 332 g (2.48 mole=50% excess) of diethylene glycol monoethyl ether. The reaction mixture was refluxed for two hours. The boiling point at the beginning was 160° C., and it dropped in the course of the reaction to 125° C.

Then, after cooling, the ethanol and the excess glycol ether were distilled off as in Example 1 until the temperature in the bottom of the distillation bridge was 120° C. 231 g of a raw product was obtained, of which approximately 45% consisted of tris[2-(2-ethoxy-ethoxy)ethoxy]silyl-3-aminopropane of the formula $H_2N-CH_2-CH_2-CH_2-Si[O(CH_2-CH_2-O)_2C_2H_5]_3$, which was confirmed by gas chromatography and mass spectrometry. The raw product also contained a total of about 35%, by weight, of the corresponding mono- and diglycol ether esters of the aminosilane.

EXAMPLE 4

Transesterification of Gamma-aminopropyltriethoxysilane with Triethylene Glycol Monoethyl Ether As in Example 1, 133 g (0.6 mol) of gamma-aminopropyltriethoxysilane was transesterified with 481 g (2.7 mol=50% excess) of triethylene glycol monoethyl ether. The reaction mixture was refluxed for 2 hours. The boiling temperature was approximately 140° C.

The distillation of the ethanol and of the unreacted glycol ether was performed as in Example 1, to a temperature of 170° C. at the bottom of the distillation bridge.

The bottom product of 330 g contained approximately 155 g of transesterification product of the formula $$H_2N-CH_2-CH_2-CH_2-Si[O-(CH_2-CH_2-O)_3-C_2H_5]_3$$

as well as the corresponding mono-and di-esterified silyl compounds. The glycol content was about 20% by weight.

EXAMPLE 5

Transesterification of Gamma-aminopropyltriethoxysilane with Triethylene Glycol Monoethyl Ether As in Example 1, 177 g (0.8 mol) of gamma-aminopropyltriethoxysilane was transesterified with 427 g (2.4 mol) of triethylene glycol monoethyl ether. 2 g of ethyl titanate was added as catalyst to the reaction mixture. The mixture was refluxed for four hours, the boiling point being approximately 124° C.

The ethanol and excess glycol ether were distilled out by first heating the reaction mixture, as in Example 1, at standard pressure to an internal temperature of 160° C., and then, after cooling, heating it in a vacuum of 10 mbar to a temperature of about 150° C.

482 g of was obtained of a raw product of which 50% by weight consisted of the same triester as in Example 4.

EXAMPLE 6

Transesterification of Gamma-aminopropylmethyldiethoxysilane with Diethylene Glycol Monomethyl Ether As in Example 1, 191 g (1 mol) of gamma-aminopropylmethyldiethoxysilane was transesterified with 360 g (3 mol=50% excess) of diethylene glycol monomethyl ether. The reaction mixture was refluxed for 2 hours. The boiling temperature was 125° C. at the beginning, and in the course of the reaction it dropped to 120° C.

Then the ethyl alcohol and unreacted diethylene glycol monomethyl ether were distilled off as in Example 1, the distillation of the glycol ether being carried to a bottom temperature of 140° C. 298 g of a yellow raw product was obtained, which still contained about 3% of glycol ether.

With this procedure the product was bis[2-(2-methoxyethoxy)-methoxy]methylsilyl-3-aminopropane of the formula $H_2N-CH_2-CH_2-CH_2-Si(CH_3)[O-(CH_2-CH_2-O)_2-CH_3]_2$ in a yield of about 12%; the corresponding mono-esterified product was obtained in the amount of about 70%.

EXAMPLE 7

Transesterification of N-methyl-gamma-aminopropyltrimethoxysilane with Diethylene Glycol Monomethyl Ether As in Example 1, 290 g (1.5 mol) of N-methyl-gamma-aminopropyltrimethoxysilane was transesterified with 810 g (6.75 mol=50% excess) of diethylene glycol monomethyl ether. The reaction mixture was refluxed for two hours. The boiling temperature was 115° C. at the start, and in the course of the reaction it fell to 105° C.

After the reaction had taken place the alcohol and the glycol ether were distilled out, the latter to a bottom temperature of 130° C. The raw product obtained in a quantity of 658 g consisted to about 67% of tris[2-(2-methoxyethoxy)-ethoxy]silyl-3-N-methylaminopropane of the formula $NH(CH_3)-CH_2-CH_2-CH_2-Si[O(CH_2-CH_2O)_2CH_3]_3$, which was confirmed by gas chromatography and mass spectrometry. The raw product furthermore contained about 70 g of undistilled glycol ether and partially transesterified products.

EXAMPLE 8

Transesterification of Gamma-mercaptopropyltri Methoxysilane with Diethylene Glycol Monomethyl Ether As in Example 1, 157 g (0.8 mol) of gamma-mercaptopropyltrimethoxysilane was transesterified with 432 g (3.6 mol=50% excess) of diethylene glycol monomethyl ether. The reaction mixture was refluxed for two hours. The reaction was catalyzed with one gram of ethyl titanate. The boiling temperature was about 106° C.

The distillation of the methanol that was formed and of the glycol ether was performed under the same conditions as in Example 1, except that, in the distillation of the glycol ether, the internal temperature was increased to 140° C. 353 g of a raw product was obtained, which consisted to about 85% by weight of tris[2-(2-methoxyethoxy)-ethoxy]silyl-3-mercaptopropane of the formula

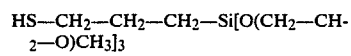

$HS-CH_2-CH_2-CH_2-Si[O(CH_2-CH_2-O)CH_3]_3$ which was confirmed by gas chromatography. The raw product also contained about 35 g of glycol ether.

EXAMPLE 9

Transesterification of Gamma-glycidyloxypropyltrimethoxysilane with Diethylene Glycol Monomethyl Ether In the apparatus described in Example 1, 118 g (0.5 mol) of gamma-glycidyloxypropyltrimethoxysilane was stirred for 8 hours at 70° C. together with 180 g (1.5 mol) of diethylene glycol monomethyl ether, in the presence of 1 g of ethyl titanate as catalyst. The methyl alcohol that was formed and the excess glycol ether were then distilled out in a vacuum of 10 mbar after cooling to room temperature and replacing the reflux condenser with a distillation bridge. The internal temperature in the meantime was increased to only 75° C. and held at this level for one hour. A raw product was obtained in a yield of 98% by weight.

EXAMPLE 10

In accordance with German Pat. No. 2,521,841, a single-component polyurethane sealing composition was prepared from the following components:
80 parts of linear isocyanate propolymer
205 parts of branched isocyanate prepolymer
120 parts of latent hardeners
100 parts of hydrophobated silicic acid
550 parts of diisodecyl phthalate
380 parts of chalk
100 parts of Shellsol T Samples of this sealing composition were modified as follows:
Sample 1: Standard for comparison: no silane added
Sample 2: Sealing composition with the addition of 0.8 wt % of gamma-aminopropyltriethoxysilane
Sample 3: Sealing composition containing 0.8 wt % of the silane ester from Example 1.

Two concrete test specimens measuring 50×15×25 mm were cemented together with these samples at a distance of 15 mm apart. The specimens were stored at 23° C. and 50% relative humidity. After 2.5 and 7 days, the traction test of DIN 52455 was performed, and the following values were obtained:

| Sealing composition | Storage time in days | Elongation in percent | Tensile N/cm² |
| --- | --- | --- | --- |
| Sample 1 | 2 | 0 | 0 |
| Sample 2 | 2 | 250 | 20.3 |
| Sample 3 | 2 | 350 | 20.0 |
| Sample 1 | 5 | 0 | 0 |
| Sample 2 | 5 | 190 | 23 |
| Sample 3 | 5 | 355 | 46 |
| Sample 1 | 7 | 0 | 0 |
| Sample 2 | 7 | 150 | 21.3 |
| Sample 3 | 7 | 370 | 50.4 |

It will be understood that the specification and examples are illustrative but not limitative of the present invention and that other embodiments within the scope of the invention will suggest themselves to those skilled in the art.

What is claimed is:

1. An organosilane ester of the formula $$Y-(CH_2)_n-Si(CH_3)_m X_p Z_{3-(m+p)},$$

wherein
Y is —SH;

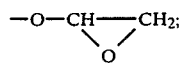

the grouping —NH—(CH$_2$)$_2$—NH—(CH$_2$)$_2$—NH$_2$; or NHR where R is H, C$_{1-6}$ alkyl, phenyl or —(CH$_2$)$_2$—NH$_2$ X is —OCH$_3$, —OC$_2$H$_5$ or —OC$_3$H$_7$, Z is —O—(CH$_2$—CH$_2$O)$_q$—R' where q is 2 or 3 and R' is an alkyl of 1 to 4 carbon atoms and one of the H-atoms can be substituted by a methyl group, and m is 0, 1 or 2; n is 1,2 or 3; and p is 0 or 1; with the proviso that m+p are equal to 0, 1 or 2.

2. The ester of claim 1 wherein n is 3.
3. The ester of claim 1 wherein m+p equal 0.
4. The ester of claim 1 wherein m+p equal 1.
5. The ester of claim 1 wherein m+p equal 2.
6. The ester of claim 1 wherein Y is NHR and R is H.
7. The ester of claim 1 wherein Y is NHR and R is C$_{1-6}$ alkyl.
8. The ester of claim 1 wherein Y is NHR and R is phenyl.
9. The ester of claim 1 wherein Y is NHR and R is —(CH$_2$)$_2$—NH$_2$.
10. The ester of claim 1 wherein Y is SH.
11. The ester of claim 1 wherein Y is

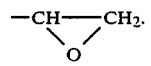

12. The ester of claim 1 wherein Y is NH—(CH$_2$)$_2$—NH—(CH$_2$)$_2$—NH$_2$.